United States Patent [19]

Miller, Jr. et al.

[11] 4,187,902

[45] Feb. 12, 1980

[54] HEAT EXCHANGE APPARATUS

[75] Inventors: Clarence S. Miller, Jr., Kennett Square, Pa.; Richard A. Hager, Wilmington, Del.

[73] Assignee: Hercofina, Wilmington, N.C.

[21] Appl. No.: 188,834

[22] Filed: Oct. 13, 1971

[51] Int. Cl.² .............................................. F28F 9/00
[52] U.S. Cl. .................................... 165/76; 422/201; 165/158; 165/162; 122/32
[58] Field of Search ................ 165/72, 74, 76, 157, 165/107, 108, 158–160, 163; 23/283, 288 E, 288 L; 122/32

[56] References Cited

U.S. PATENT DOCUMENTS

| | | | |
|---|---|---|---|
| 1,617,519 | 2/1927 | Hartmann | 165/163 UX |
| 2,199,216 | 4/1940 | Conti | 165/163 X |
| 2,973,944 | 3/1961 | Etter | 165/145 |
| 3,065,061 | 11/1962 | Fett | 23/283 |
| 3,171,477 | 3/1965 | Huet | 122/32 X |
| 3,227,142 | 1/1966 | Bell et al. | 122/34 |
| 3,700,030 | 10/1972 | Busquain | 165/163 |

FOREIGN PATENT DOCUMENTS

| | | | |
|---|---|---|---|
| 1097551 | 2/1955 | France | 165/158 |
| 286554 | 2/1965 | Netherlands | 122/32 |
| 678211 | 8/1952 | United Kingdom | 123/283 |
| 950727 | 2/1964 | United Kingdom | 165/163 |

*Primary Examiner*—Samuel M. Scott
*Assistant Examiner*—Theophil W. Streule, Jr.
*Attorney, Agent, or Firm*—George H Hopkins

[57] ABSTRACT

Disclosed is an apparatus for exchanging heat with liquid material and particularly liquid material under superatmospheric pressure. A preferred embodiment of the apparatus comprises a pressure vessel for holding a body of the liquid material, and having an inlet and an outlet for the liquid material. Inside the vessel is an integral tube assembly for conducting heat exchange fluid into, through and out of a body of the liquid material in the vessel. The tube assembly comprises a heat exchange fluid feed header, a heat exchange fluid discharge header, and a plurality of heat transfer tubes from the feed header to the discharge header. In a preferred embodiment of the apparatus, the headers are coaxially aligned with a normally vertical axis, and are vertically spaced apart. The headers are joined to conduits passing through the top and bottom of the vessel. These conduits in combination with the vessel support the tube assembly. The heat transfer tubes are generally in longitudinally extending radial planes and occupy an arc about said normally vertical axis preferably greater than 270°, but less than 360°, whereby a wedge shaped longitudinally extending space is provided for access to the backside of the tubes and to the region of the axis. The ends of the heat transfer tubes are joined to lateral ports in the headers. Preferably, each heat transfer tube has an elbow section in the bottom portion thereof in the region of the bottom header, that extends upwardly at an angle to an intersecting radius, which is obtuse, the purpose of which is to minimize sagging of the tube. Also, preferably each heat transfer tube has a laterally offset portion between the bottom and top portions, for the purpose of taking up stresses induced by thermal expansion. In fabricating, transporting and installing the tube assembly, the two headers preferably are fastened to the opposite ends of a removable rigid support piece which is removed after the tube assembly has been installed in the vessel.

3 Claims, 4 Drawing Figures

HEAT EXCHANGE APPARATUS

This invention relates to ways and means for exchanging heat with a body of liquid material.

The liquid phase oxidation of p-xylene and methyl p-toluate with molecular oxygen is a highly exothermic reaction. Commercially it is carried out on a continuous basis under superatmospheric pressure in a reactor which in essence is a pressure vessel having within its interior a plurality of heat conductive tubes through which a heat exchange fluid is passed for removing heat from the body of liquid material undergoing reaction in the vessel. The tubes are generally vertically disposed in the vessel. However, heretofore each end portion of each tube bends laterally and extends through openings in the vessel side wall with one end being connected to an externally positioned heat exchange fluid supply manifold, and the other end being connected to an externally positioned heat exchange fluid discharge manifold. An example of such a reactor is disclosed in the U.S. Pat. No. 3,065,061, to Fett.

A reactor so constructed, however, presents many difficulties in fabrication, maintenance and repair, which are magnified with increases in size of the reactor. Indeed, the larger the reactor, the more impractical is this construction.

The apparatus described herein, however, substantially minimizes, if not avoids, a number of these difficulties.

The heat exchange apparatus disclosed in this specification comprises: (1) vessel means for containing a body of liquid material to be heat exchanged, and comprising means for introducing liquid material into said body and for withdrawing liquid material from said body; (2) an integral tube assembly for conducting heat transfer fluid into, through and out of said body, said tube assembly being inside of said vessel means and comprising heat transfer fluid feed header means, heat transfer fluid discharge header means, and a plurality of heat conductive tubes for conveying heat exchange fluid in heat exchange relationship with said body from said feed header means to said discharge header means; and (3) conduit means extending from said header means inside said vessel means to the exterior of said vessel means for conveying heat exchange fluid to and from said heat exchanger. Preferably the integral tube assembly is supported by the vessel means in combination with the conduit means extending from both of the header means.

In a preferred embodiment of the heat exchanger the header means are coaxially aligned on a normally vertical axis and are spaced from each other.

The tubes are arranged generally parallel to that axis and preferably the open ends of the tubes are joined to lateral ports in the header means. Consequently, the tubes have a generally longitudinal portion and at each end lateral sections joined to the corresponding lateral ports of the two headers. Preferably the tubes are arranged in longitudinally disposed radial planes about the normally vertical axis of the assembly in an arc substantially less than 360°, but desirably more than 270°, whereby space is provided for access to the backside of said tubes as well as access to the axial region of the assembly.

Preferably the tubes have such a high longitudinal length to diameter ratio that sag and thermal expansion or contraction must be taken into account. Consequently, in a preferred embodiment each heat conductive tube has an elbow section between its bottom lateral section and its generally longitudinal portion. The elbow section is at an obtuse angle to an intersecting radius from the longitudinal axis of the tube assembly. The obtuse angle preferably is less than 135°. Also, the top lateral section is substantially at right angles to the generally longitudinal portion. Also, each section or portion of the tube that merges into another section or portion of the tube does so at a minimum radius of curvature. These aspects minimize sag. To take care of thermal expansion or contraction, the longitudinal portion of each tube has a laterally offset portion which preferably is offset in the laterally disposed radial plane in which the tube is generally positioned.

An advantage of the heat exchange apparatus disclosed herein is that the integral tube assembly can be fabricated apart from the vessel means, and subsequently installed in the vessel means. When this is done, the preferred embodiment of integral tube assembly comprises a rigid support member removably fastened at opposite ends to the feed header means and discharge header means. The rigid support or core member minimizes transverse and longitudinal stressing of the tube assembly during the fabrication, transportation and installation in the vessel means. After installation, the rigid support member is unfastened and removed via the access space from the tube assembly.

The best mode now contemplated for carrying out the invention is exemplified by the apparatus illustrated in the drawings which form a material part of these disclosures. In the drawings.

Figure 1:
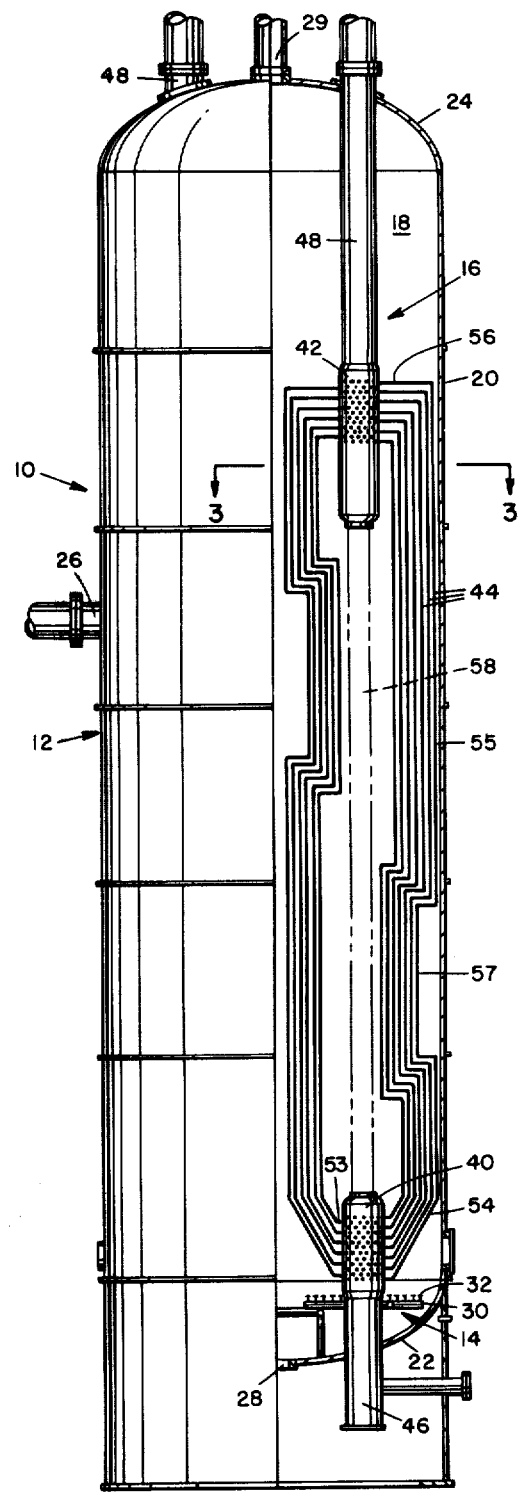
FIG. 1 is an elevation in partial section of a preferred specific embodiment of the heat exchanger apparatus of this specification.

In greater detail, FIG. 1 depicts a heat exchange apparatus 10 which is particularly useful as a reactor for continuously carrying out a highly exothermic reaction between a gas and a component of liquid material, in which reaction there might be a tendency for deposition of a solid such as a catalyst or a product of reaction. An example of such a reaction is the liquid state oxidation of p-xylene and methyl p-toluate with molecular oxygen with the aid of an oxidation catalyst. The apparatus 10 comprises a pressure vessel 12, a gas sparger assembly 14 and a heat exchange tube assembly 16.

The pressure vessel 12 comprises a cylindrical chamber 18 with a normally vertical axis, which is formed by a cylindrical casing 20 with an inverted dome bottom 22 and a dome top 24 joined together in a pressure tight relationship and capable of withstanding superatmospheric pressures that are established and maintained under selected normal operative conditions. The axial dimension of the cylindrical chamber 18 is several times greater than the diameter of the chamber. The cylindrical casing 20 has a feed port 26 through which liquid material to be treated is introduced. The bottom 22 of the vessel 12 comprises an outlet port 28 for withdrawing treated liquid material from the vessel. The top 24 of the vessel 12 has a spent gas outlet 29.

The gas sparger assembly 14, only part of which is shown in FIG. 1, comprises in the region of the bottom 22 a plurality of pipes 30 joined to a pressurized gas distribution system (not shown) and arranged generally transversely relative to the axis of the cylindrical chamber 18. Each of the pipes 30 has a plurality of nozzles 32 through which gas is introduced into the body of liquid material established and maintained in the cylindrical chamber 18.

The heat exchange tube assembly 16 comprises a heat exchange fluid feed header 40, a heat exchange fluid discharge header 42 and a plurality of heat conductive tubes 44 extending between the two headers 40 and 42.

Figure 4:
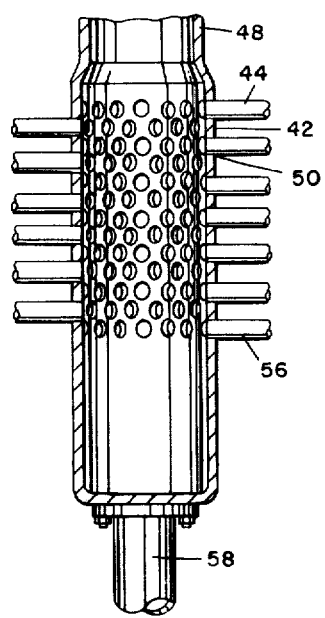
FIG. 4 is a section of the top header of the tube assembly in the apparatus of FIG. 1, which section is taken as indicated by the sectioning plane 4—4 in FIG. 2.
Figure 2:
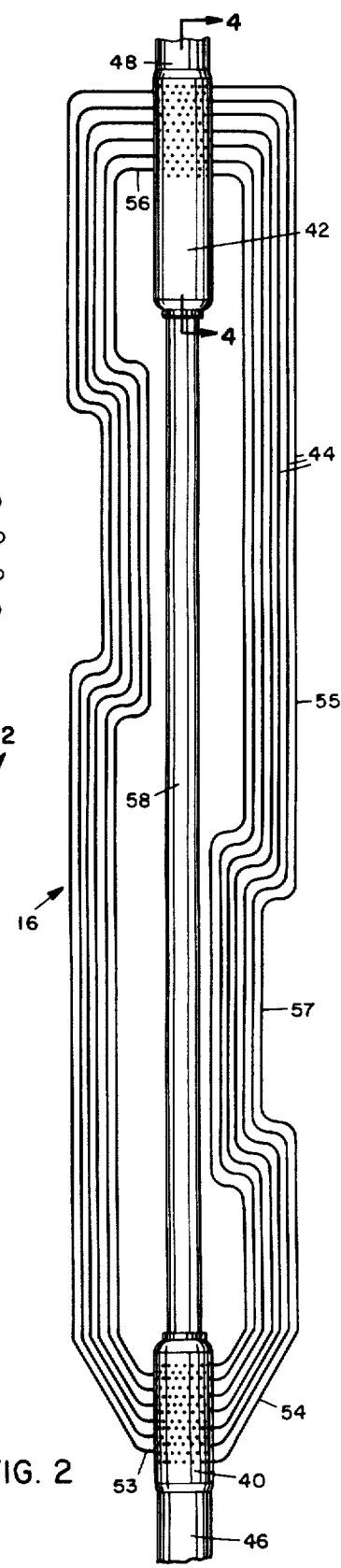
FIG. 2 is an enlarged elevation of the tube assembly of the apparatus prior to installation.

The two headers are coaxially aligned with the normally vertical axis of the tube assembly 16. The feed header 40 is joined to a feed conduit 46 which, as can be seen in FIGS. 1, 2 and 4, is rigid longitudinally and laterally, extends in pressure tight relationship through the bottom 22 of the vessel 12 and in combination with the bottom 22 anchors and supports the bottom portion of the tube assembly 16. The discharge header 42 is joined to a discharge conduit 48 which, as can be seen in FIGS. 1, 2 and 4, is rigid longitudinally and laterally, extends in pressure tight relationship through the top 24 of the vessel 12 and in combination with the top 24 anchors and supports the top portion of the tube assembly 16.

Figure 3:
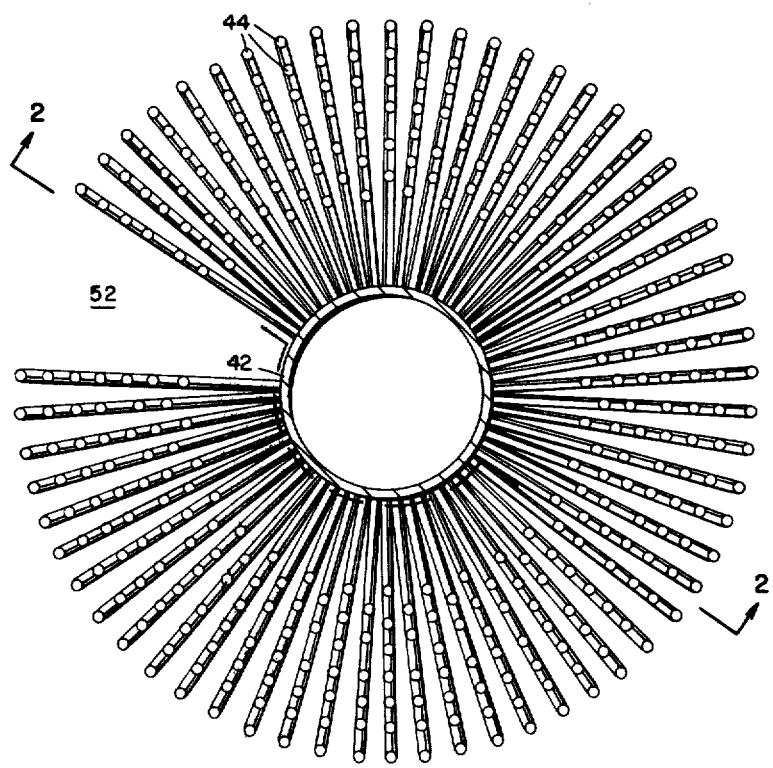
FIG. 3 is a plan section view taken as indicated by the view plane 3—3 in FIG. 1.

The heat conductive tubes 44 in general are disposed parallel to the normally vertical axis of the tube assembly 16. However, as best shown in FIG. 4 the ends of the tubes 44 are seated in pressure tight relationship in lateral openings or ports 50 in the two headers 40 and 42. In the embodiment shown (see FIG. 3), the tubes 44 are arranged in parallel in series in a plurality of longitudinally disposed radial planes circumferentially equidistantly spaced from each other in an arc about the axis of the assembly 16 substantially less than 360° and preferably greater than 270°, whereby access space 52 is provided. This longitudinal space gives access to the backside of each series or bank of tubes 44 for maintenance and repair, as well as access to the axial region of the assembly. Because of the close circumferential spacing between adjacent banks of tubes (see FIG. 3), the lateral openings 50 in the two headers 40 and 42 corresponding to adjacent banks of tubes 44 are staggered longitudinally (see FIG. 4).

As depicted in FIGS. 1 and 2, each heat conductive tube 44 has a large length to diameter ratio. To minimize sag, therefore, the bottom end portion of each tube in the region of the corresponding lateral port 50 of the feed header 40 has a lateral end section 53, the open end of which is seated in the lateral port 50 and the other end of which merges with a minimum radius of curvature into an elbow section 54. The elbow section 54 is at an angle obtuse to an intersecting radius from the longitudinal axis of the tube assembly 16. Preferably the obtuse angle is less than 135°, but larger and smaller angles can be employed in other embodiments of the assembly. The upper end of the elbow section 54 merges with a minimum radius of curvature into the generally longitudinal portion 55 of the tube. In addition, the upper end portion of each tube 44 has a lateral end section 56 generally perpendicular to the longitudinal axis of the assembly 16, the open end of which is seated in the corresponding lateral port 50 of the top or discharge header 42, and the other end of which merges with a minimum radius of curvature into the generally longitudinal portion 55 of the tube.

When the heat exchange tube assembly 16 is placed into normal operation, it undergoes thermal expansion. In other embodiments of the apparatus intended for operation at or near atmospheric pressure, an expansion joint between the top or heat exchange fluid discharge conduit 48 and the top 24 of the vessel 12 can be employed to take care of the thermal expansion of the tube assembly 16. In the embodiment of the apparatus shown in the drawings, however, each heat conductive tube 44 in its generally longitudinal portion 55 has a laterally offset section 57 (see FIGS. 1 and 2) to take up the stresses induced by thermal expansion.

When the heat exchange tube assembly 16 is fabricated, preferably the two headers 40 and 42 are fastened as by bolts (see FIG. 4) to the opposite ends of a removable rigid support piece 58 as in FIG. 2 (shown in FIG. 1 in relief). The support piece 58 minimizes longitudinal and transverse stressing of the tubes 44 in the fabrication of the heat exchange tube assembly 16, transportation of the assembly 16 from a remote fabrication site to the place of installation of the apparatus 10, and in the installation of the assembly 16 in the vessel 12. When the heat exchange tube assembly 16 is installed in the vessel 12, the rigid support piece 58 is unfastened from the two headers 40 and 42, removed via the access space 52 from the assembly 16, and removed from the vessel 12 as by way of a normally closed manhole (not shown) in the top 24 of the vessel 12.

Under normal operative conditions a body of liquid material (for example, p-xylene, methyl p-toluate and oxidation catalyst) is established and maintained in the vessel 12 by continuously introducing liquid material into the vessel through feed port 26, and by continuously withdrawing liquid material including reaction product or products (for example, p-toluic acid and monomethyl terephthalate) through the outlet port 28. The quiescent height of the body of liquid is generally such that there is a sufficient space at the top end region of the chamber 18 for spent gas to collect and be withdrawn with a minimum of liquid material. The tube assembly 16 is usually positioned so that most, if not all, of the longitudinal portion 55 of each heat conductive tube 44 is immersed in the body of liquid material. Reactive gas (for example, air) is continuously introduced into the reactor 12 by way of the gas sparger assembly 14. Spent gas reaching the top of the vessel 12 is withdrawn from the reactor through the spent gas outlet 29. In the meantime, heat exchange fluid (for example, water) is passed through the feed conduit 46 to the feed header 40 through the heat conductive tubes 44 into the discharge header 42 and out the discharge conduit 48. The discharged heat exchange fluid can be disposed of or recycled after removal of heat.

While the flow of heat exchange fluid through the heat exchange tube assembly 16 has been described as in the upward direction in the apparatus of the drawings, it can be in the opposite direction if desired.

Also, while the apparatus 10 has been described in the context of an exothermic reaction, it also can be used as a reactor for endothermic reactions.

A feature of advantage of the heat exchange tube assembly 16 is that under normal operative conditions with copious quantities of reactive gas passing upwardly through the body of liquid material in the vessel 12, the tubes 44, because of their high length to diameter ratio, are free to flex and vibrate with the currents of gas and liquid material. This is a distinct advantage when the body of liquid material contains a substance that tends to precipitate. In such case the flexing or vibration of the tubes 44 tends to minimize of precipitate on the tubes.

Another feature of advantage of the heat exchange tube assembly 16, is that it does not limit the size of the vessel. A vessel of any size can be employed, and depending on what is needed or desired in the way of heat exchange, any number of heat exchange tube assemblies 16 can be employed. Hence, the vessel 12 can be custom-built according to the requirements of a specific situation, while the heat exchange tube assembly or assemblies can be standardized.

Other features, advantages, and specific embodiments of the invention will become readily apparent to those exercising ordinary skill in the art after reading the foregoing disclosures. These specific embodiments are within the scope of the claimed subject matter unless otherwise expressly indicated to the contrary. Also, while a specific embodiment of the invention has been described in considerable detail, variations and modifications of this embodiment can be effected without departing from the spirit and scope of the invention as disclosed and claimed.

While the apparatus 10 has been described in the context of a superatmospheric pressure operation, it also can be used in subatmospheric pressure operations.

Claimed are:

1. A transportable integral heat exchanger tube assembly for the interior of a chemical reactor for continuously carrying out a highly thermic chemical reaction involving liquid material, copious quantities of a gas and a reaction mixture comprising a readily precipitable substance that tends to deposit on heat exchange tubes in contact with the reaction mixture under normal operative conditions, which reactor comprises vessel means for containing a body of said reaction mixture, which assembly comprises: heat transfer fluid feed header means; heat transfer fluid discharge header means axially aligned on a normally vertical longitudinal axis with and longitudinally spaced from said discharge header means; a plurality of heat conductive tubes from said feed header means to said discharge header means, said heat conductive tubes (a) having such high length to diameter ratio as to be flexible and vibratable by currents of gas and liquid in said body to thereby minimize deposition of precipitate on said tubes under normal operative conditions, and (b) being in longitudinally disposed radial planes about said axis in an arc substantially less than 360°, whereby space is provided for access to the back side of said tubes; for conveying heat transfer fluid to and from said header means and in combination with vessel means for supporting and anchoring in position in said vessel means said integral tube assembly, longitudinally and laterally rigid longitudinally outwardly extending feed conduit means in combination with said feed header means, and longitudinally and laterally rigid longitudinally outwardly extending discharge conduit means in combination with said discharge header means; and rigid support means on said axis between and fastened to said feed header means and said discharge header means for minimizing longitudinal and transverse stressing of said heat conductive tubes in the fabrication, transportation and installation of said assembly, said rigid support means being removable from said feed header means and said discharge header means after said assembly has been installed in said vessel means.

2. An integral heat exchanger tube assembly according to claim 1 in which said arc is at least 270°.

3. An integral heat exchanger tube assembly according to claim 2 in which the ends of said heat conductive tubes are joined to lateral ports in said header means.

* * * * *